United States Patent [19]
Elliott

[11] Patent Number: 6,001,059
[45] Date of Patent: Dec. 14, 1999

[54] OTOSCOPE RETROFIT TO ALLOW MULTIPURPOSE USE

[76] Inventor: Peter Christopher Elliott, No. 2 Lakeside, Austin, Tex. 78746

[21] Appl. No.: 09/306,210

[22] Filed: May 6, 1999

Related U.S. Application Data

[63] Continuation-in-part of application No. 09/080,894, May 18, 1998.

[51] Int. Cl.[6] .................................................. A61B 1/227
[52] U.S. Cl. .......................................... 600/184; 600/200
[58] Field of Search .................... 600/200, 199, 600/187, 185, 184; 606/162

[56] References Cited

U.S. PATENT DOCUMENTS

| | | | |
|---|---|---|---|
| 1,693,021 | 11/1928 | Cameron | 600/200 |
| 2,039,546 | 5/1936 | McGerry | 600/200 |
| 3,146,775 | 9/1964 | Moore et al. | 600/200 |
| 3,596,653 | 8/1971 | Hotchkiss | 600/200 |
| 3,812,847 | 5/1974 | Moore et al. | 600/200 |
| 3,958,566 | 5/1976 | Furihata . | |
| 4,006,738 | 2/1977 | Moore et al. . | |
| 4,380,998 | 4/1983 | Kieffer, III et al. . | |
| 5,209,219 | 5/1993 | Hollobaugh . | |
| 5,390,663 | 2/1995 | Schaefer . | |
| 5,454,817 | 10/1995 | Katz | 606/106 |
| 5,916,150 | 6/1999 | Sillman | 600/200 X |

FOREIGN PATENT DOCUMENTS

| | | | |
|---|---|---|---|
| 2566668 | 1/1986 | France | 600/200 |
| 2185688 | 7/1987 | United Kingdom | 600/200 |

*Primary Examiner*—Jeffrey A. Smith
*Attorney, Agent, or Firm*—Joseph F. Long

[57] ABSTRACT

An otoscope retrofit speculum extension with a sidearm thereon connectable to a vacuum source to pull a vacuum in the interior of said retrofit extension to pull and to hold a foreign body against an end of said extension to allow removal of foreign bodies from an ear or a nose by removal of the otoscope.

6 Claims, 2 Drawing Sheets

US 6,001,059

OTOSCOPE RETROFIT TO ALLOW MULTIPURPOSE USE

This is a continuation-in-part of Ser. No. 09/080,894, filed May 5, 1998, inventor P. C. Elliott entitled "An otoscope retrofit to allow multipurpose use" (pending).

BACKGROUND

An otoscope is an instrument normally designed to allow a physician to peer inside an ear or into a nose through a lighted pathway. At times, particularly in infants, there are foreign bodies such as a bead within an ear or nose that necessitate removal. The objectives of this invention include low cost retrofitting of an otoscope to allow removal of foreign material from a nose and ear in a rapid patient comfortable manner.

The invention includes about one eighth inch diameter flexible plastic tubing with a first end connectable to a controllable vacuum source and a second end leading to and connectable to a sidearm on the speculum in one embodiment and connectable to a sidearm on speculum extensions or retrofits in other embodiments. An insufflation port on the head of the otoscope may be partially or totally closed using finger pressure to engage or disengage the vacuum source. Normally with no external vacuum source the physician uses a small air bulb and finger pressure to vibrate the tympanic membrane in the inner ear to determine if there is fluid behind the tympanic membrane. In the invention size of the insufflation port and control of the vacuum source are such that with the insufflation port totally open there is essentially no vacuum in the otoscope. The invention includes embodiments of the retrofitting units for attachment to the speculum receptacle or holder of the otoscope wherein the user may controllably pull vacuum through the retrofit units to hold a foreign body against the retrofit unit for removal and prevent foreign material from entering the otoscope head.

In all embodiments the speculum or the foreign body remover extensions are so formed with sidearm projections or ribs (not shown in the drawings) as to prevent in use sealing of the retrofitted speculum against the outer ear and to prevent subsequent tympanic membrane damage from the vacuum.

Minor changes to the speculum or the speculum retrofit units of the otoscope would be easily made but would be within the purview of the invention. We wish to be limited only to the spirit and purpose as outlined in these specifications and claims.

SUMMARY OF THE INVENTION

The invention encompasses simple low cost removable additions or retrofit units to allow use of a vacuum source and a users thumb or finger pressure to adjustably pull a vacuum in the interior of an otoscope retrofit unit without interfering with the users line of sight to inspect an interior of an ear or a nose. When a foreign body is detected in an ear or nose a retrofit unit is attached to the otoscope unit speculum receptacle. The retrofit unit is inserted into the cavity close to the foreign body, and a vacuum is applied to hold the foreign body against the remover extension unit thereby allowing easy painless removal by simply disengaging the otoscope.

In preferred embodiments for foreign body removal the vacuum source for the otoscope ties into the retrofit units and lowered pressure or vacuum in the retrofit unit may be separated from atmospheric pressure in the otoscope head.

DESCRIPTION OF THE INVENTION

Figure 1:
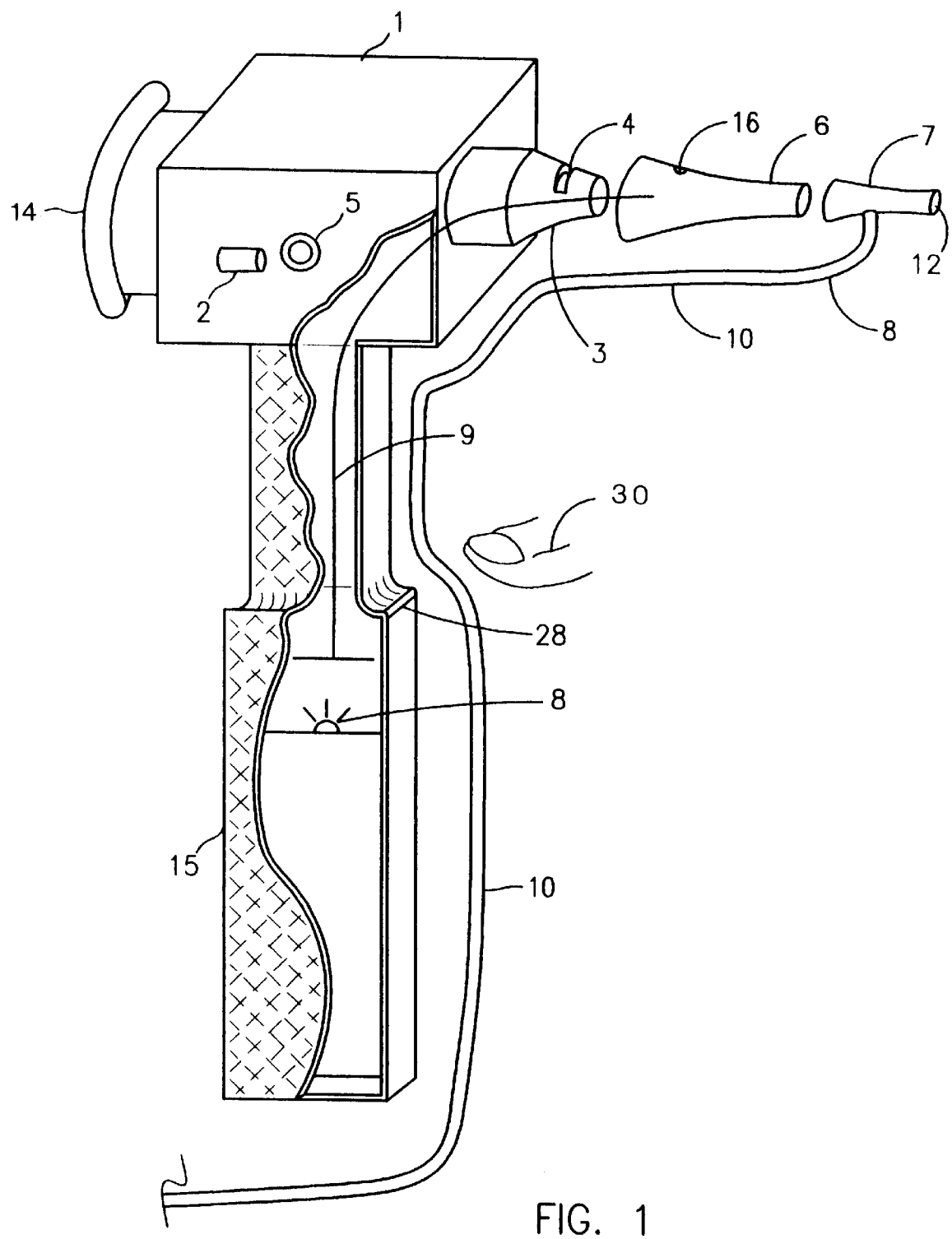
FIG. 1 shows an otoscope wherein a vacuum source is connectable with the retrofit unit that is an extension of the speculum.

The invention may best be described from the drawings. In FIG. 1 an otoscope 1 head with an insufflation port 5 and handle 15 is shown. An electrically powered light 8 with a fiber optic bundle 9 furnishes light to the distal end of the cone shaped speculum receptacle or holder 3 through the speculum 6 and, if the retrofit unit 7 is installed through the retrofit extension 7 so that a viewer may inspect an interior of an ear or nose by looking through lens 14. The speculum 6 may be twistably connected with the speculum holder 3 with ridge 16 twisting into slot 4. The retrofit unit 7 may be frictionally held on speculum 6. The retrofit unit 7 is preferably made with a semi-rigid plastic to allow the tip 12, which may be flared or otherwise shaped, to more easily fit partially around and seal against a foreign body when a vacuum is pulled inside the unit 7. To pull a vacuum inside unit 7 a distal end of a flexible plastic tube 10 is connected to sidearm 8 with a beginning end of plastic tube 10 removably connected with a vacuum source. Finger pressure 30 may be used to pinch line 10 against an edge such as 28 on the otoscope handle to effectively control the vacuum in extension 7. In hospitals the house vacuum could be used but low cost, low volume, light weight diaphragm pumps are readily available. With the vacuum connector line 10 connected to sidearm 8 and the extension 7 in place a physician user may place the shaped tip 12 against a foreign body in the ear or nose and use finger pressure to create a vacuum in the otoscope head 1, speculum 6, and speculum extension 7 thereby allowing removal of the foreign body by simply withdrawing the otoscope while continuing to hold the vacuum in the retrofit unit 7 to hold the foreign body against tip 12. A plastic or rubber plug 2 may be used to close insufflation port 5 when using the retrofit units as shown in FIG. 1 and FIG. 2; when using a cuplike unit 26, FIG. 3 to separate the pressure in the otoscope head from the pressure in the retrofit unit plugging the insufflation port is not necessary.

Figure 2:
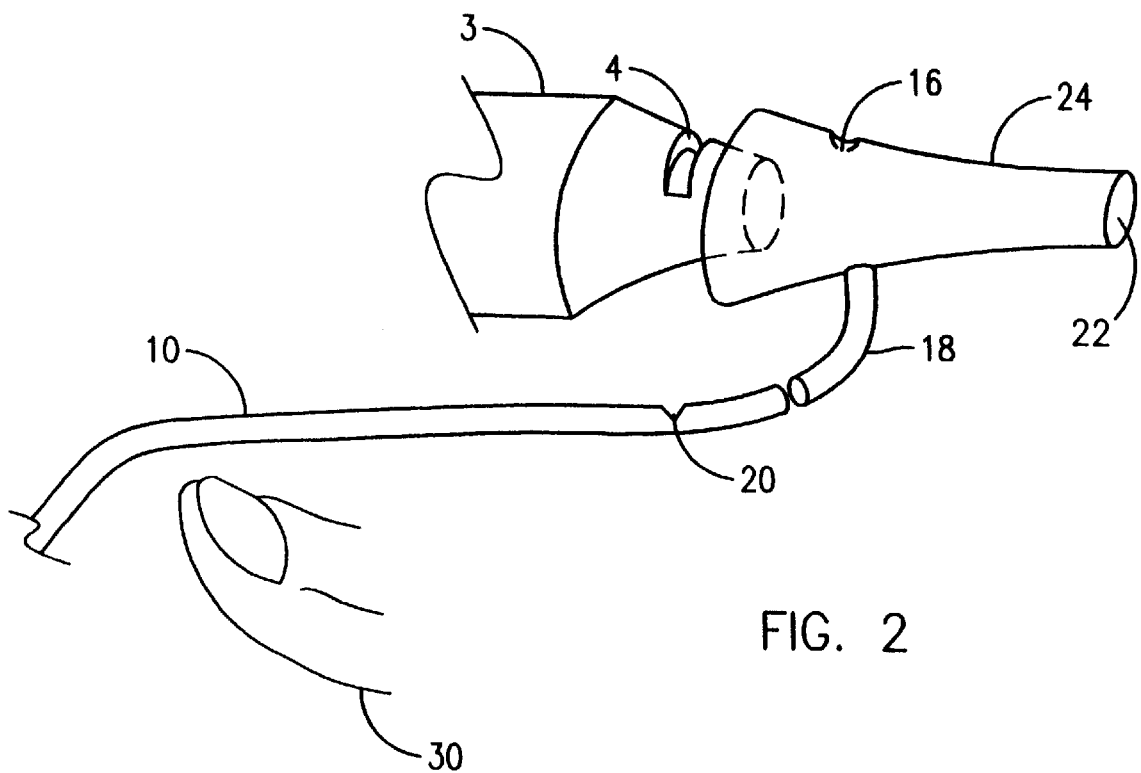
FIG. 2 shows a second embodiment with the vacuum source connectable into the speculum and controllable with a vacuum port.

In FIG. 2 a second retrofit type unit is a speculum 24 made with a semi-rigid plastic with a thin shaped end 22 and an air removal sidearm 18 connectable with the plastic tube 10 which is connected with a vacuum source. A "V" notch or port in line 10 may be either partially or totally closed with finger pressure 30 bending line 10 thereby controlling the vacuum in retrofit unit 24. This allows holding the reduced pressure or vacuum in unit 24 to hold a foreign body against flared or shaped end 22 and to remove said foreign body by simply removing the otoscope.

Figure 3:
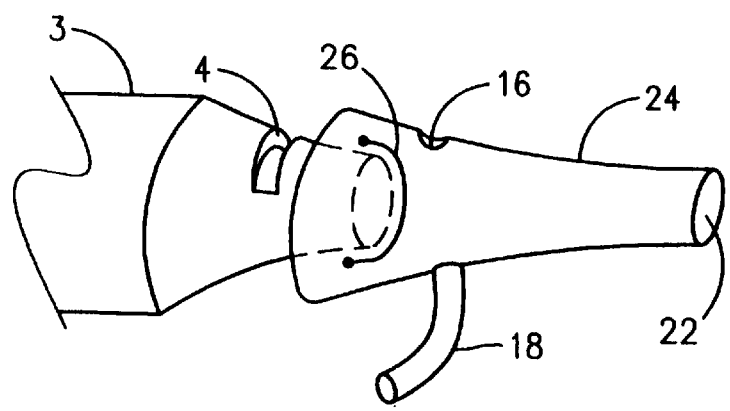
FIG. 3 shows a clear plastic cup to isolate pressure within the otoscope head from pressure within the retrofit extension.

FIG. 3 shows an embodiment exactly similar to the embodiment in FIG. 2 with a clear bottom cuplike unit 26 covering the end of the speculum receptacle 3. With the cuplike unit 26 in place the pressure in the otoscope head is separated from the pressure in the retrofit units. The cuplike unit 26 may be used with retrofit embodiments shown in both FIG. 1 and FIG. 2.

In all embodiments the speculum and any connectors may be fabricated from any of several semi-rigid plastics or rubber with a heat sterilizable plastic being preferred. Depending on the vacuum source used a needle valve adjustment, not shown, may be necessary in line 10 for optimum operation of the otoscope and the retrofit units. Tips 22 are shown as flared but straight tips and varying shaped tips mat also be used for removing irregular shaped foreign bodies.

What is claimed is:

1. A retrofit kit to allow multipurpose use of an otoscope comprising:
   a) an extension for a speculum on said otoscope, said extension having an open sidearm and a shaped end,
   b) a vacuum connector tube with a first end operably connectable with an exterior vacuum source; and with a second end operably fixably connectable to said open sidearm on said extension.

2. The retrofit kit to allow multipurpose use of an otoscope as in claim 1 further comprising a cuplike plastic unit with a clear bottom fittable over a distal end of said speculum receptacle inside said speculum when said speculum is installed on said speculum receptacle.

3. A retrofit kit to allow multipurpose use of an otoscope comprising:
   a) a cone shaped unit attachable to a speculum receptacle on a head of said otoscope;
   b) a sidearm open to an interior of said cone shaped unit and formed at a point below a tip end of said speculum receptacle when said cone shaped unit is installed on said speculum receptacle,
   c) a vacuum connector tube with a first end operably connectable with an exterior vacuum source; and with a second end operably fixably connectable to said sidearm on said cone shaped unit.

4. The retrofit kit to allow multipurpose use of an otoscope as in claim 3 further comprising a cuplike plastic unit with a clear bottom fittable over a distal end of said speculum receptacle inside said cone shaped unit when said cone shaped unit is installed on said speculum receptacle.

5. A retrofit kit to allow multipurpose use of an otoscope comprising:
   a) a cone shaped unit attachable to a speculum receptacle on a head of said otoscope;
   b) a sidearm open to an interior of said cone shaped unit and formed at a point below a tip end of said speculum receptacle when said cone shaped unit is installed on said speculum receptacle,
   c) a vacuum connector tube with a first end operably connectable with an exterior vacuum source; and with a second end operably connectable to said sidearm on said cone shaped unit;
   d) a V shaped port in said vacuum connector tube at a point in said second end just below said operable connection to said sidearm with said V shaped port being closeable by using finger pressure to bend said vacuum connector tube toward a handle of said otoscope.

6. The retrofit kit to allow multipurpose use of an otoscope as in claim 1 wherein said vacuum connector tube is fabricated from a sufficiently pliable plastic that finger pressure may be used to effectively close said tube thereby allowing finger pressure control of said vacuum in said extension.

* * * * *